United States Patent
Nakase et al.

(10) Patent No.: US 11,285,195 B2
(45) Date of Patent: Mar. 29, 2022

(54) PHARMACEUTICAL COMPOSITION FOR INHIBITING EXPRESSION OF CD47 IN TUMOR CELLS AND USE OF SAME

(71) Applicants: TOAGOSEI CO., LTD., Tokyo (JP); OSAKA PREFECTURE UNIVERSITY PUBLIC CORPORATION, Osaka (JP)

(72) Inventors: Ikuhiko Nakase, Sakai (JP); Kosuke Noguchi, Sakai (JP); Nahoko Baileykobayashi, Tsukuba (JP); Tetsuhiko Yoshida, Tsukuba (JP)

(*) Notice: Subject to any disclaimer, the term of this patent is extended or adjusted under 35 U.S.C. 154(b) by 545 days.

(21) Appl. No.: 15/881,452

(22) Filed: Jan. 26, 2018

(65) Prior Publication Data
US 2018/0214528 A1 Aug. 2, 2018

(30) Foreign Application Priority Data
Jan. 27, 2017 (JP) .............................. JP2017-013140

(51) Int. Cl.
*A61K 39/00* (2006.01)
*A61K 9/127* (2006.01)
*A61K 35/36* (2015.01)
*A61K 35/54* (2015.01)

(52) U.S. Cl.
CPC ...... *A61K 39/001129* (2018.08); *A61K 9/127* (2013.01); *A61K 35/36* (2013.01); *A61K 35/54* (2013.01)

(58) Field of Classification Search
CPC ......... A61P 35/00; A61K 9/127; A61K 35/12; A61K 9/0087
See application file for complete search history.

(56) References Cited

U.S. PATENT DOCUMENTS

| | | | |
|---|---|---|---|
| 6,685,911 B1* | 2/2004 | Zitvogel | A61P 35/00 424/1.21 |
| 9,186,405 B2* | 11/2015 | Rak | A61K 45/06 |
| 10,732,181 B2* | 8/2020 | Nagai | G01N 33/57488 |
| 2017/0246304 A1* | 8/2017 | Nakase | A61P 35/00 |
| 2018/0104187 A1* | 4/2018 | Liu | A61K 31/7105 |

FOREIGN PATENT DOCUMENTS

| JP | 2007008895 A | 1/2007 |
|---|---|---|
| JP | 2015536351 A | 12/2015 |

OTHER PUBLICATIONS

Kumar et al, Current Pharmaceutical Designs, 2015, vol. 21, 10 pages. (Year: 2015).*
Koh et al (Biomaterials, 2017, vol. 121, pp. 121-129) (Year: 2017).*
Zeringer et al (World Journal of Methodology, 2013, vol. 3, pp. 11-18) (Year: 2013).*
Paolini et al (Biochemistry, 2017, vol. 56, pp. 6401-6408) (Year: 2017).*
Shtam et al (Cell Communication and Signaling, 2013, vol. 11, 10 pages) (Year: 2013).*

* cited by examiner

*Primary Examiner* — Karen A. Canella
(74) *Attorney, Agent, or Firm* — Lambert Shorten & Connaughton; David J. Connaughton, Jr.; Justin P. Tinger (57) ABSTRACT

The pharmaceutical composition for inhibiting expression of CD47 in tumor cells provided by the present invention contains:
  exosomes produced by cultured tumor cells in an amount effective for inhibiting expression of the CD47; and
  a pharmaceutically acceptable carrier.

6 Claims, 4 Drawing Sheets

PHARMACEUTICAL COMPOSITION FOR INHIBITING EXPRESSION OF CD47 IN TUMOR CELLS AND USE OF SAME

CROSS-REFERENCE TO RELATED APPLICATIONS

The present application claims priority on the basis of Japanese Patent Application No. 2017-013140 filed on Jan. 27, 2017, the contents of which are incorporated herein by reference.

TECHNICAL FIELD

The present invention relates to a pharmaceutical composition containing an effective amount of a substance produced by cells for inhibiting expression of CD47 in tumor cells. In addition, the present invention relates to a method for inhibiting expression of CD47 in tumors cells by using this composition.

TECHNICAL BACKGROUND

CD47 is a type of protein present in the cell membrane of tumor cells, and as is indicated by its being referred to as the "don't eat me signal", is known to allow tumor cells (including breast cancer cells, ovarian cancer cells, uterine cancer (including cervical cancer and endometrial cancer, to apply similarly hereinafter) cells, prostate cancer cells, bladder cancer cells, colon cancer cells, liver cancer cells, squamous cell carcinoma cells or brain tumor cells) to avoid attack by macrophages, dendritic cells and other immune cells by expressing large amounts of CD47 therein (phagocytosis, etc.).

Thus, inhibiting expression of CD47 in and/or on tumor cells (cancer cells) is an extremely important approach from the viewpoint of being able to enhance the efficacy of immunotherapy against tumor cells (cancer cells). For example, development is proceeding on an antitumor pharmaceutical composition for the purpose of blocking CD47 by administering anti-CD47 antibody to patients. For example, Japanese Patent Application Laid-open No. 2007-8895 and WO 2014/087248 disclose an example of a pharmaceutical composition having anti-CD47 antibody as the main component thereof (antitumor pharmaceutical composition).

However, in the case of an antitumor agent that uses anti-CD47 antibody as described above, it is difficult to effectively inhibit the activity of CD47 expressed in large amounts in the cell membrane of tumor cells, thus requiring further enhancement of the action and effects thereof in the case of using this antibody.

SUMMARY OF THE INVENTION

The present invention employs a completely different approach from the antitumor approach using anti-CD47 antibody described above, and has as the object thereof the providing of a method for making it easier for immune cells to attack tumor cells (through phagocytosis and the like) by inhibiting the expression per se of CD47 in tumor cells, as well as the providing of a material (pharmaceutical composition) used in that method.

In order to realize the above-mentioned objects, the pharmaceutical composition for inhibiting expression of CD47 in tumor cells disclosed herein is a pharmaceutical composition (composition used in pharmacological applications), containing:

exosomes produced by cultured tumor cells in an amount effective for inhibiting expression of the CD47; and a pharmaceutically acceptable carrier.

Exosomes are membrane vesicles having a diameter of about 20 nm to 200 nm that are secreted from various cells in the body or cultured cells, and are known to contain various proteins, lipids or nucleic acids such as RNA there within.

The inventor of the present invention surprisingly found that the expression of CD47 by tumor cells can be prominently inhibited by supplying exosomes recovered from a medium containing tumor cells cultured in vitro to the target tumor cells, thereby leading to completion of the present invention.

Namely, together with the pharmaceutical composition disclosed herein, the present invention provides a method for inhibiting expression of CD47 in tumor cells, which includes supplying exosomes produced by separately cultured tumor cells to target tumor cells in an amount effective for inhibiting expression of CD47.

According to the pharmaceutical composition and method for inhibiting expression of CD47 disclosed herein, the amount of CD47 produced in target tumor cells (as well as tumor tissue composed of those cells) can be reduced. Consequently, the pharmaceutical composition and method for inhibiting expression of CD47 disclosed herein is able to promote the attack of these tumor cells by macrophages, dendritic cells and other immune cells (such as T cells). Thus, according to the pharmaceutical composition and method for inhibiting expression of CD47 disclosed herein, the efficacy of cancer immunotherapy against these tumor cells can be improved.

In a preferable aspect of the pharmaceutical composition and method for inhibiting expression of CD47 disclosed herein, the above-mentioned cultured tumor cells (above-mentioned tumor cells cultured for the purpose of producing exosomes) are any of squamous cell carcinoma cells and uterine cancer cells.

Exosomes derived from cultured cells of these types of cancer are able to preferably inhibit expression of CD47 by target tumor cells (such as squamous cell carcinoma cells, uterine cancer cells, breast cancer cells, ovarian cancer cells, prostate cancer cells, bladder cancer cells, colon cancer cells, lung cancer cells, liver cancer cells, squamous cell carcinoma cells, brain tumor cells, lymphoma cells or myeloma cells).

In addition, in another preferable aspect of the pharmaceutical composition and method for inhibiting expression of CD47 disclosed herein, the above-mentioned cultured tumor cells (above-mentioned tumor cells cultured for purpose of producing exosomes) are derived from the tumor cells that are the target of inhibiting expression of CD47 as described above.

The production of CD47 in target tumor cells (as well as tumor tissue composed of those cells) can be reduced by using exosomes produced and recovered by culturing the same tumor cells as the target tumor cells (or tumor cells acquired from the target tumor tissue). In addition, since the use of exosomes obtained from the same tumor cells as the target tumor cells (or tumor cells acquired from the target tumor tissue) makes it possible to reduce the risk associated with an immune reaction, this aspect is preferable for carrying out the method for inhibiting expression of CD47 not only in vitro, but also in vivo.

In addition, in another preferable aspect of the pharmaceutical composition disclosed herein, the above-mentioned exosomes include exosomes isolated from a culture broth of the above-mentioned cultured tumor cells by ultracentrifugation. Similarly, another preferable aspect of the method for inhibiting expression of CD47 disclosed herein uses exosomes isolated from a culture broth of the above-mentioned cultured tumor cells for the above-mentioned exosomes.

The use of exosomes isolated by ultracentrifugation makes it possible to effectively reduce the amount of CD47 produced in target tumor cells (as well as tumor tissue composed of those cells).

DESCRIPTION OF THE PREFERRED EMBODIMENTS

The following provides an explanation of preferred embodiments of the present invention. Matters other than those specifically mentioned in the present description that are necessary for carrying out the invention (such as general matters relating to cell culturing methods or preparation of pharmaceutical compositions) can be understood to be design matters for a person with ordinary skill in the art based on the prior art in fields such as cellular engineering, physiology, medicine, pharmacy, organic chemistry or biochemistry. The present invention can be carried out based on the contents disclosed in the present description and common general technical knowledge in the relevant fields.

In the present description, "exosomes" refer to vesicles formed by a lipid bilayer membrane secreted extracellularly from various eukaryotic cells. Although exosomes are typically vesicles having a diameter of about 20 nm to 200 nm, there are no particular limitations on the size or form thereof provided they are produced by cultured tumor cells.

Exosomes used as the main component of the pharmaceutical composition disclosed herein are recovered after having been excreted from various cultured tumor cells. For example, exosomes can be used after having cultured tumor cells, such as breast cancer cells, ovarian cancer cells, uterine cancer cells, prostate cancer cells, bladder cancer cells, colon cancer cells, liver cancer cells, squamous cell carcinoma cells, brain tumor cells, lymphoma cells or myeloma cells, for a prescribed amount of time in ordinary media followed by recovering from the media and purifying according to various methods. For example, routinely available (and typically, commercially available) cultured tumor cell lines, such as HeLa cells derived from human cervical cancer cells or A431 cells derived from human squamous cell carcinoma cells, can be preferably used to produce exosomes.

There are no particular limitations on the culturing conditions of the cultured tumor cells or media constituent materials selected for use in carrying out the present invention provided they conform to conventionally recommended conditions and media constituent materials corresponding to the type of cultured tumor cells used. For example, media can be used that has been prepared by adding components such as FBS or other serum and antibiotics and the like as necessary to commercially available media such as DMEM, MEM, α-MEM, GMEM or Ham's F-12 medium.

Although there are no particular limitations thereon, from the viewpoint of efficiently recovering an adequate amount of exosomes with few contaminants, the culturing period is preferably such that, after culturing for about 2 days to 7 days under temperature conditions of about 37° C. using serum-containing media not containing serum-derived animal exosomes in a $CO_2$-rich atmosphere (having a $CO_2$ concentration of, for example, about 5%), the exosomes are isolated and recovered from the culture broth.

A conventionally known method can be employed to recover exosomes from culture broth. For example, exosomes can be isolated and recovered by the conventionally commonly used ultracentrifugation method (see, for example, Thery, C., *Curr. Protoc. Cell Biol.* (2006), Chapter 3: Unit 3.22).

Alternatively, exosomes can also be isolated and recovered from a culture broth by, for instance, FACS, ultrafiltration, gel permeation, filtration, HPLC or a method involving adsorption of a polymer, beads or the like. Exosomes may also be isolated and recovered using a commercially available exosome isolation reagent (or kit). For example, desired exosomes can be isolated and recovered by purchasing an exosome isolation kit from Cosmo Bio Co., Ltd.

Preferably, exosomes are isolated and recovered based on ultracentrifugation. According to this method, all of the exosomes are reliably recovered by preventing outflow of a specific component (for which recovery is difficult). Although there are no particular limitations thereon, after removing contaminants by several stages of preliminary centrifugation at a centrifugal force of, for example, about 300×g to 10,000×g (such as by centrifuging for 5 minutes to 20 minutes at 300×g, for 5 minutes to 20 minutes at 2,000×g and for 20 minutes to 30 minutes at 10,000×g under conditions of 4° C.), by then carrying out ultracentrifugation for about 60 minutes to 90 minutes (overnight ultracentrifugation according to experimental conditions) at a centrifugal force of about 100,000×g to 200,000×g, highly pure exosomes can be obtained with few contaminants.

Recovery of exosomes according to a method described above (such as ultracentrifugation) enables confirmation by observing the exosomes using a transmission electron microscope (and typically, negative staining) or by method for detecting a marker protein (such as CD9, CD63 or CD81) by a technique such as western blotting, ELISA or FACS (and typically, an immunological technique). In addition, exosome-derived RNA may also be measured.

Furthermore, since recovered exosomes per se can be said to be a mixture of various compounds, it is difficult or unrealistic to express the total amount thereof in terms of weight. Consequently, in the present description, the amount of exosomes is expressed as the total amount of protein contained in the exosomes. Namely, the amount of recovered exosomes (g) can be treated as the total amount of protein measured in a dispersion of the recovered exosomes. More specifically, in the case 1 μg/mL of total protein is contained in a dispersion of recovered exosomes, 1 μg/mL of exosomes can be considered to be contained in the exosome dispersion.

There are no particular limitations on the target for carrying out (applying) the pharmaceutical composition disclosed herein, or in other words, the target for carrying out the method for inhibiting expression of CD47 disclosed herein, in the form of target tumor cells provided they are tumor cells. For example, tumor cells such as breast cancer cells, ovarian cancer cells, uterine cancer cells, prostate cancer cells, bladder cancer cells, colon cancer cells, liver cancer cells, squamous cell carcinoma cells, brain tumor cells, lymphoma cells or myeloma cells, or tumor tissue composed of tumor cells, are applicable (as targets). The pharmaceutical composition or method for inhibiting expression of CD47 disclosed herein may be carried out against tumor cells that have been subcultured in vitro or cultured temporarily (or against tissue composed of those cells), or may be carried out against tumor cells (or tissue composed of those cells) in vivo (namely, within the body of a patient).

The pharmaceutical composition disclosed herein can contain various pharmacologically (medically) allowable carriers corresponding to the form of use thereof provided the composition contains an effective amount of the active component thereof in the form of exosomes without losing the activity thereof that inhibits expression of CD47. For example, carriers able to be commonly used in peptide drugs, such as diluents or excipients, can be applied.

Although able to be suitably varied corresponding the application and form of the pharmaceutical composition disclosed herein, typical examples of carriers include water, phosphate-buffered saline (PBS) and various organic solvents. The carrier can also be an aqueous solution containing a suitable concentration of an alcohol (such as ethanol), glycerol, or a non-drying oil such as olive oil. Alternatively, the carrier may also consist of liposomes. In addition, examples of secondarily contained components include various fillers, thickeners, binders, humectants, surface activators, pigments and fragrances.

From the viewpoint of inhibiting expression of CD47 in tumor cells, the pharmaceutical composition disclosed herein can also be referred to as an antitumor composition or antitumor agent. Examples of typical forms thereof include liquids, suspensions, emulsions, aerosols, foams, granules, powders, tablets, capsules, ointments and aqueous gels. In addition, the pharmaceutical composition disclosed herein can also be in the form of a freeze-dried product or granulated susbstance for the purpose of preparing a pharmaceutical solution by dissolving in physiological saline or a suitable buffer (such as PBS) immediately before use in order to use for injection and the like.

Furthermore, the process per se for preparing various forms of pharmaceutical compositions is only required to comply with a conventionally known method, and since that production method per se does not characterize the present invention, a detailed explanation thereof is omitted. An example of a detailed source of information relating to formulation is Comprehensive Medicinal Chemistry, Corwin Hansch, ed., Pergamon Press (1990). The entire contents of this publication are incorporated in the present description by reference.

The pharmaceutical composition disclosed herein can be used in a form, method or dosage corresponding to the objective thereof.

For example, in the case of using for the purpose of supplying exosomes to tumor cells (or tissue composed of those cells) cultured in vitro (outside the body), an effective and suitable amount of exosomes is added to the target tumor cells (or tissue) in any stage of the culturing process (such as at an early stage after the start of culturing, or after having cultured (grown) or subcultured the cells for a prescribed amount of time).

There are no particular limitations on the amount of exosomes added or the number of times exosomes are added since these parameters can vary according to conditions such as the type of tumor cells, cell density (cell density at the start of culturing), passage number, culturing conditions or type of medium. In terms of the effective amount thereof, exosome concentration in the medium is generally preferably about 5 μg/mL or more and more preferably 10 μg/mL or more. On the other hand, there is the possibility of having an effect on other physiological activity if exosomes are supplied in an excessively large amount, thereby making this undesirable. Although there are no particular limitations thereon, the suitable exosome concentration in a medium is generally about 5 μg/mL to 100 μg/mL, and preferably about 10 μg/mL to 50 μg/mL (for example, 20 μg/mL to 30 μg/mL). Exosomes are preferably added multiple times (such as at an interval from one to two additions/day to one addition/day to 2 days) in order to allow the effect of inhibiting expression of CD47 to persist for a fixed period of time or longer.

Alternatively, the pharmaceutical composition disclosed herein can also be administered in a desired amount to a patient (namely, to the body of patient, or in vivo). There are no particular limitations on the administration method. Examples of administration methods include intravenous, intraarterial, intradermal, subcutaneous or intraperitoneal injection, oral administration, inhalation, transmucosal administration and suppository administration. A means for administering directly to the affected area (tumor cells or tumor tissue composed of those cells) is particularly preferable. For example, the pharmaceutical composition disclosed herein may be administered by implanting an implanted preparation subcutaneously or submuscularly.

Furthermore, the organism targeted for application of the pharmaceutical composition and method for inhibiting expression of CD47 disclosed herein can be a human or animal other than a human (and typically, a mammal) Targeting a human is particularly preferable due to the high value thereof for the health care industry. In addition, targeting a test animal such as a mouse, rat, guinea pig, rabbit, dog or cynomolgus monkey for application of the pharmaceutical composition and method for inhibiting expression of CD47 disclosed herein is preferable from the viewpoint of promoting various research and development. In addition, targeting pets such as dogs or cats for application is preferable due to the high utility value in the veterinary medicine industry.

In the case of administering the pharmaceutical composition disclosed herein to a human or other body, it is necessary to ensure safety as well as reduce an immune reaction to the administered exosomes and composition containing those exosomes.

From this viewpoint, the cultured tumor cells (exosome production source) used is preferably of the same species as the target tumor cells (and tumor tissue). For example, in the case of introducing an exogenous substance into human tumor cells, it is preferable to use exosomes produced by human-derived cultured tumor cells. An example of an aspect related thereto consists of using the target for inhibiting expression of CD47 in the form of cells derived from tumor cells for the cultured tumor cells (cultured tumor cells for producing exosomes). For example, in the case of targeting human breast cancer cells or breast cancer tissue composed of those cells, cells can be preliminarily harvested from the breast cancer tissue followed by culturing the cells and using the exosomes produced by those cells.

Although the following provides an explanation of several examples relating to the present invention, the present invention is not intended to be limited to that indicated in the examples.

Test 1: Production and Recovery of Exosomes

In this test, a total of three types of cell lines indicated below were acquired and used as cultured cells for producing exosomes.

(1) HeLa cells (established cell line derived from human cervical cancer cells)

(2) A431 cells (established cell line derived from human squamous cell carcinoma cells)

(3) CHO-K1 cells (established cell line derived from Chinese hamster ovaries)

Among the above-mentioned cell lines, the HeLa cells of (1) were acquired from the Cell Engineering Division of the RIKEN BioResource Center. The A431 cells of (2) and the CHO-K1 cells of (3) were acquired from the U.S. ATCC. Each of the acquired cell lines were cultured using α-MEM medium (GIBCO Corporation) for (1), using MEM medium (GIBCO Corporation) for (2), and using Ham's F-12 medium (GIBCO Corporation) for (3). The cell lines were subcultured at 37° C. under conditions of 5% $CO_2$ after adding FBS to the media to a concentration of 10%.

Suitable amounts of the above-mentioned corresponding media containing FBS at a concentration of 10% (FBS removed of serum-derived animal exosomes) were then added to culture dishes having a diameter of 100 mm followed by disseminating any of the cells lines described in (1) to (3) above therein at $3\times10^6$ cells/dish. The cells were then cultured for 3 days at 37° C. under conditions of 5% $CO_2$.

Following completion of culturing for 3 days, the culture broth was recovered and subjected to ultracentrifugation to isolate and recover exosomes. More specifically, each culture broth was continuously centrifuged as indicated below under conditions of 4° C. Namely, the recovered culture broth was centrifuged for 10 minutes at 300×g followed by recovery of the supernatant and centrifuging for 10 minutes at 2,000×g. Next, the supernatant was recovered and centrifuged for 30 minutes at 10,000×g followed by recovering the supernatant and subjecting to two rounds of ultracentrifugation for 70 minutes each at 100,000×g.

Following completion of the above-mentioned ultracentrifugation, the sediment was dispersed in PBS and recovered. A dispersion of exosomes derived from the above-mentioned HeLa cells of (1), a dispersion of exosomes derived from the above-mentioned A431 cells of (2), and a dispersion of exosomes derived from the above-mentioned CHO-K1 cells of (3) were obtained.

The concentrations of the recovered exosomes were determined by treating total protein concentration (μg/mL), quantified using the Pierce® BCA Protein Assay Kit (Thermo Fisher Scientific Inc.), as exosome concentration (μg/mL). The exosome concentration of each exosome dispersion was adjusted by suitably diluting with PBS in preparation for testing to be subsequently described.

Test 2: Supply of Exosomes to Target Tumor Cells and Measurement of Amount of CD47 Produced (Expressed)

In this test, a total of three types of cell lines indicated below were acquired and used as target tumor cells that supply exosomes.

(A) HeLa cells (established cell line derived from human cervical cancer cells)
(B) A431 cells (established cell line derived from human squamous cell carcinoma cells)
(C) MDA-MB-231 cells (established cell line derived from human breast cancer)

Among the above-mentioned cell lines, the HeLa cells of (A) and the A431 cells of (B) are respectively the same cell lines as the above-mentioned cultured tumor cells for producing exosomes in the form of the HeLa cells of (1) and the A431 cells of (2). In addition, the MDA-MB-231 cells of (C) were acquired from the U.K. ECACC. Each of the acquired cell lines were cultured using α-MEM medium (GIBCO Corporation) for (A) and using MEM medium (GIBCO Corporation) for (B) and (C). The cell lines were subcultured at 37° C. under conditions of 5% $CO_2$ after adding FBS to the media to a concentration of 10%.

Suitable amounts of the above-mentioned corresponding media containing FBS at a concentration of 10% were then added to each well of commercially available 24-well microplates (Iwaki & Co., Ltd.) followed by disseminating any of the tumor cells previously described in (A) to (C) therein at $1.4 \times 10^5$ cells/well. The cells were then cultured for 24 hours at 37° C. under conditions of 5% $CO_2$.

Following completion of culturing for 24 hours, a dispersion of exosomes derived from the above-mentioned HeLa cells of (1), a dispersion of exosomes derived from the above-mentioned A431 cells of (2), and a dispersion of exosomes derived from the above-mentioned CHO-1 cells of (3) were added to each well (600 μg/well). At this time, the exosome concentration in each well (as protein concentration) was made to be 5 μg/mL or 20 μg/mL. In addition, a well to which 600 μL of medium only containing 10% FBS was added without containing exosomes was used as a comparative control (0 μg/mL).

Following addition of the exosome dispersions (or medium only containing 10% FBS without containing exosomes), the cells were cultured for 24 hours at 37° C. under conditions of 5% $CO_2$. Next, each of the wells was washed with serum-free Ham's F-12 followed by investigating the effects of addition or non-addition of exosomes, or the difference in exosome concentrations in the case of exosome addition groups, on the amount of CD47 produced (expressed) according to the fluorescent antibody method using anti-CD47 antibody (B6H12, Santa Cruz Biotechnology, Inc.). The following provides a detailed description thereof.

200 μL of a solution containing the above-mentioned antibody (4 μg/mL) were added to each well following the above-mentioned washing followed by allowing to stand undisturbed for 30 minutes at 4° C. Next, 200 μL of a solution containing goat anti-mouse IgG (4 μg/mL) (Invitrogen Corporation), serving as a secondary antibody labeled with a fluorescent dye in the form of Alexa Fluor® 488, were added followed by allowing to stand undisturbed for 30 minutes at 4° C.

Following completion of the reaction, the cells present in the wells were washed with PBSs and then treated for 10 minutes at 37° C. with 200 μL of 2 mM EDTA followed by the addition of 200 μL of PBS to the wells and recovering the contents (cells) of the wells.

Next, 400 μL of the recovered material (cells) were introduced into a flow cytometer (Guava® easyCyte, Merck Millipore Ltd.).

Fluorescent intensity was then measured using the above-mentioned flow cytometer. More specifically, fluorescent intensity equivalent to 10,000 viable cells per sample was measured based on forward scattering analyses and side scattering analyses under conditions of an excitation wavelength of 488 nm and an emission wavelength of 525 nm.

Test 3: Supply of Exosomes to Target Tumor Cells and Measurement of Cell Viability Cell viability when exosomes were supplied to the above-mentioned three types of tumor cells (A) to (C) serving as targets for supply of exosomes followed by culturing the cells was measured by carrying out a cell proliferation assay by absorption spectrophotometry using WST-1 (4-[3-(4-iodophenyl)-2-(4-nitrophenyl)-2H-5-tetrazolio]-1,3-benzene disulfonate) (Water-soluble Tetrazolium Salt) (WST-1 assay). The dispersion of exosomes derived from the A431 cells of (2) above was used for the supplied exosomes. Details of the test are as described below.

Suitable amounts of the above-mentioned corresponding media containing FBS at a concentration of 10% were added to each well of commercially available 96-well microplates followed by disseminating any of the tumor cells described in (A) to (C) above therein at $1 \times 10^4$ cells/well (100 μL). The cells were then cultured for 24 hours at 37° C. under conditions of 5% $CO_2$.

Following completion of culturing for 24 hours, a dispersion of exosomes derived from the above-mentioned A431 cells of (2) were added to each well (50 μg/well). At this time, the exosome concentration in each well (as protein concentration) was made to be 5 μg/mL or 20 μg/mL. In addition, a well to which 50 μL of medium containing only 10% FBS was added without containing exosomes was used as a comparative control (0 μg/mL). After supplying exosomes to the tumor cells in the manner described above, the cells were cultured for 24 hours at 37° C. under conditions of 5% $CO_2$.

Next, the viable state (number of viable cells) of the tumor cells in each well was measured using a commercially available colorimetry kit (Premix WST-1 Cell Proliferation Assay System, Takara Bio Inc.). Namely, the number of viable cells was measured by measuring the amount of water-soluble formazan present in the medium by absorption spectrophotometry (measurement wavelength: 450 nm, reference wavelength: 620 nm) utilizing the formation of water-soluble formazan resulting from the reduction of tetrazolium salt present in the reagent due to the enzyme activity of viable cells. Furthermore, the assay was carried out as indicated in the manual provided with the above-mentioned assay kit with the exception of the procedure described in detail below.

More specifically, 10 μL/well of a reagent containing a chromogenic substrate in the form of "Water-Soluble Tetrazolium Salt (WST-1)" were added to the cell culture wells after the above-mentioned prescribed culturing time had elapsed followed by incubating for 40 minutes under conditions of 5% $CO_2$ and 37° C. Subsequently, the cell culture broths to which the chromogenic reagent had been added were measured for absorption at a wavelength of 450 nm ($A_{450}$) and absorption at a wavelength of 620 nm ($A_{620}$) using a microplate reader, the value $A_{450-620}$, obtained by correcting $A_{450}$ with $A_{620}$, was calculated, and the relative value of cell viability (%) of each test group was calculated according to the following equation based on a value of 100% for the cell viability of an exosome non-addition group: cell viability (%)=($A_{450-620}$ value of each test group)÷ ($A_{450-620}$ value of exosome non-addition group)×100.

Evaluation of CD47 Expression Inhibitory Activity and Cell Viability

The results of Test 2 and Test 3 described above were summarized in several graphs attached to the present description.

Figure 1A:
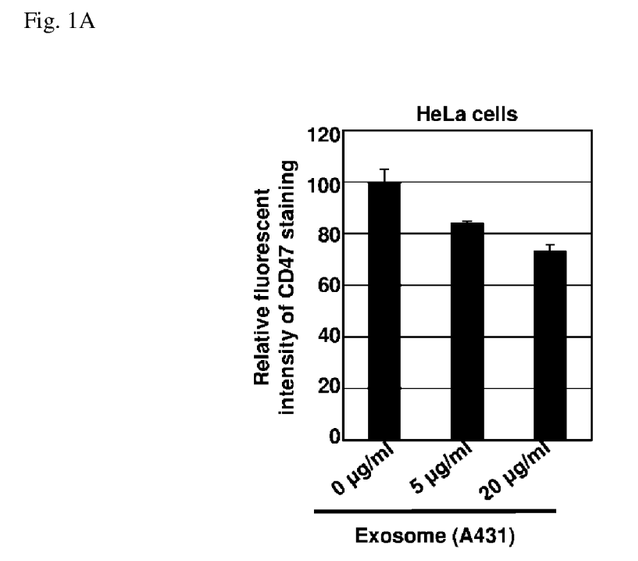
FIG. 1A is a graph investigating changes in the amount of CD47 produced after having added exosomes recovered from cultured tumor cells (A431 cells) to target tumor cells (cultured HeLa cells); in this graph, results for each concentration of exosomes (0 μg/mL, 5 μg/mL, 20 μg/mL) added during culturing of the target tumor cells (cultured HeLa cells) are indicated as relative fluorescent intensity (relative value based on an intensity of 100 for an exosome non-addition group (0 μg/mL)) based on the fluorescent antibody method (also referred to as a fluorescent immunoassay, and to apply similarly hereinafter) using anti-CD47 antibody; and average values when the same tests were independently repeated three times are indicated with the bars, and the error bars indicate standard deviation (±SD).
Figure 1B:
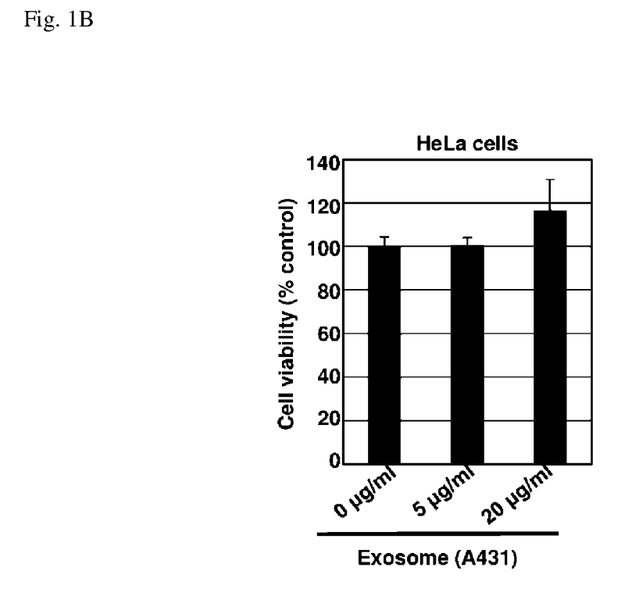
FIG. 1B is a graph investigating cell viability (%) after having added exosomes recovered from cultured tumor cells (A431 cells) to target tumor cells (cultured HeLa cells); in this graph, results for each concentration of exosomes (0 μg/mL, 5 μg/mL, 20 μg/mL) added during culturing of the target tumor cells (cultured HeLa cells) are indicated as a relative value based on viability of 100% for the cell viability of an exosome non-addition group (0 μg/mL); and average values when the same tests were independently repeated three times are indicated with the bars, and the error bars indicate standard deviation (±SD).

First, FIG. 1A is a graph investigating changes in the amount of CD47 produced (expressed) after having added exosomes derived from the A431 cells of (2) to HeLa cells. FIG. 1B is a graph investigating cell viability (%) after having added the exosomes derived from A431 cells of (2) to HeLa cells.

As is clear from the results of these graphs, the addition of exosomes derived from A431 cells was observed to make it possible to prominently inhibit expression of CD47 by cultured HeLa cells (FIG. 1A). In addition, this inhibitory activity corresponded to the amount of exosomes supplied, and concentration dependency was clearly present. On the other hand, in the case of having supplied exosomes derived from A431 cells at 20 μg/mL or more, the viability of the HeLa cells was confirmed to increase (FIG. 1B). This result indicates that, although excessive addition of exosomes enhances CD47 expression inhibitory activity, it also is able to induce an action that activates some other form of physiological activity.

Thus, in the present test, the amount of exosomes added (concentration in medium) was determined to preferably be about 5 μg/mL to 50 μg/mL.

Figure 2:
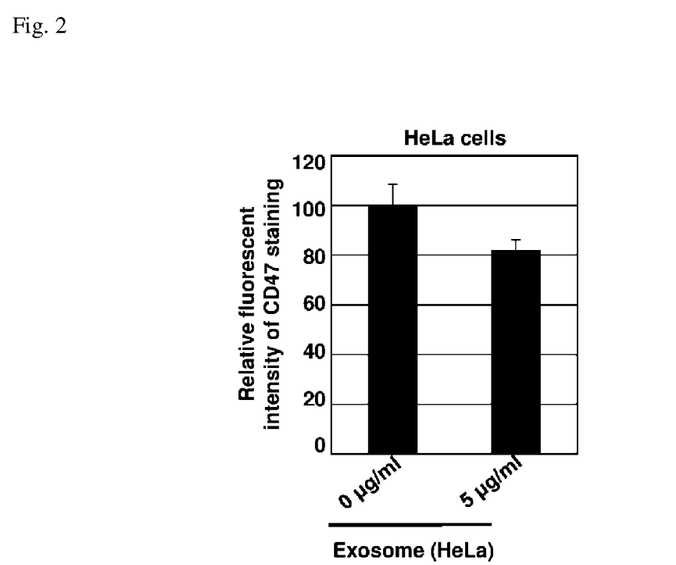
FIG. 2 is a graph investigating changes in the amount of CD47 produced after having added exosomes recovered from cultured tumor cells (HeLa cells) to target tumor cells (cultured HeLa cells) of the same type; in this graph, results for each concentration of exosomes (0 μg/mL, 5 μg/mL) added during culturing of the target tumor cells (cultured HeLa cells) are indicated as relative fluorescent intensity (relative value based on an intensity of 100 for an exosome non-addition group (0 μg/mL)) based on the fluorescent antibody method using anti-CD47 antibody; and average values when the same tests were independently repeated three times are indicated with the bars, and the error bars indicate standard deviation (±SD).

Next, FIG. 2 is a graph investigating changes in the amount of CD47 produced (expressed) after having added exosomes derived from the HeLa cells of (1) to cultured HeLa cells of the same cell line.

As is clear from the results indicated in this graph, the technology disclosed herein is capable of inhibiting expression of CD47 in target tumor cells (as well as tumor tissue composed of those cells) by culturing tumor cells (or tumor cells acquired from target tumor tissue) of the same type as the target tumor cells and using exosomes produced by and recovered from those cells. Consequently, expression of CD47 in the target tumor cells can be inhibited while reducing the risk of the occurrence of an immune reaction.

Figure 3:
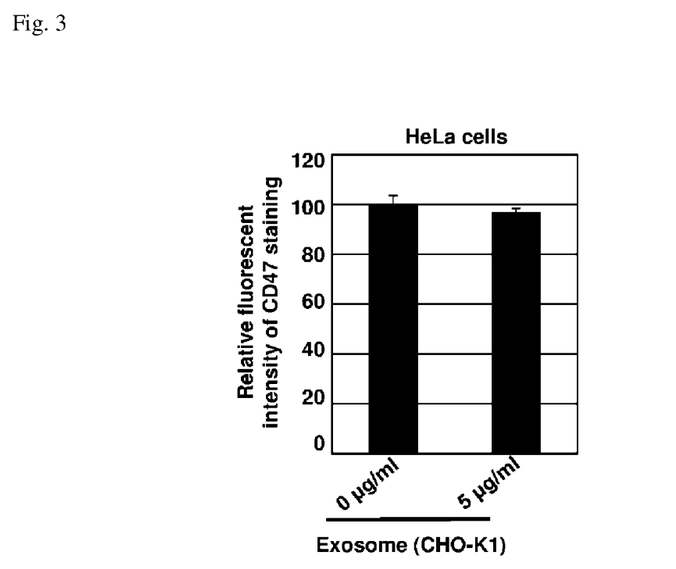
FIG. 3 is a graph investigating changes in the amount of CD47 produced after having added exosomes recovered from cultured non-tumor cells (CHO-K1 cells derived from Chinese hamster ovaries) to target tumor cells (cultured HeLa cells); in this graph, results for each concentration of exosomes (0 μg/mL, 5 μg/mL) added during culturing of the target tumor cells (cultured HeLa cells) are indicated as relative fluorescent intensity (relative value based on an intensity of 100 for an exosome non-addition group (0 μg/mL)) based on the fluorescent antibody method using anti-CD47 antibody; and average values when the same tests were independently repeated three times are indicated with the bars, and the error bars indicate standard deviation (±SD).

Next, FIG. 3 is a graph investigating changes in the amount of CD47 produced (expressed) after having added exosomes derived from the CHO-K1 cells of (3), which are non-tumor cells, to cultured HeLa cells.

Based on the results shown in this graph, exosomes derived from non-tumor cells were determined to have hardly any effect on inhibition of expression of CD47 by the target tumor cells.

Figure 4A:
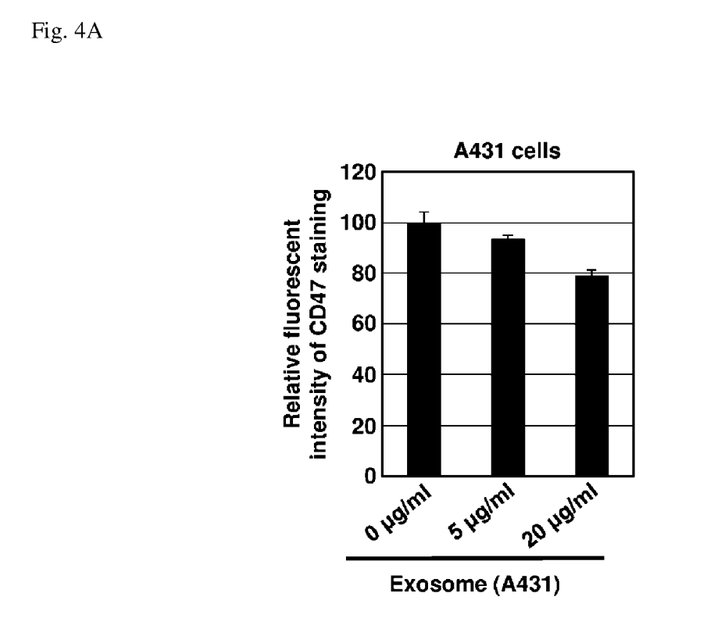
FIG. 4A is a graph investigating changes in the amount of CD47 produced after having added exosomes recovered from cultured tumor cells (A431 cells) to target tumor cells (cultured A431 cells) of the same type; in this graph, results for each concentration of exosomes (0 μg/mL, 5 μg/mL, 20 μg/mL) added during culturing of the target tumor cells (cultured A431 cells) are indicated as relative fluorescent intensity (relative value based on an intensity of 100 for an exosome non-addition group (0 μg/mL)) based on the fluorescent antibody method using anti-CD47 antibody; and average values when the same tests were independently repeated three times are indicated with the bars, and the error bars indicate standard deviation (±SD).
Figure 4B:
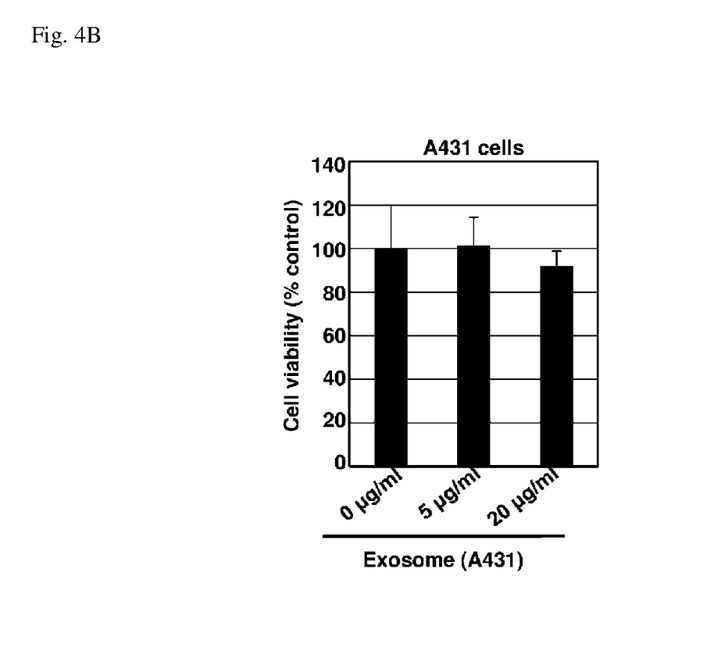
FIG. 4B is a graph investigating cell viability (%) after having added exosomes recovered from cultured tumor cells (A431 cells) to target tumor cells (cultured A431 cells) of the same type; in this graph, results for each concentration of exosomes (0 μg/mL, 5 μg/mL, 20 μg/mL) added during culturing of the target tumor cells (cultured A431 cells) are indicated as a relative value based on viability of 100% for the cell viability for an exosome non-addition group (0 μg/mL), and average values when the same tests were independently repeated three times are indicated with the bars, and the error bars indicate standard deviation (±SD).

Next, FIG. 4A is a graph investigating changes in the amount of CD47 produced (expressed) after having added exosomes derived from the A431 cells of (2) to cultured A431 cells of the same cell line. FIG. 4B is a graph investigating cell viability (%) after having added exosomes derived from the A431 cells of (2) to cultured A431 cells of the same cell line.

As is clear from the results of these graphs, with regard to the A431 cells as well, expression of CD47 in target tumor cells (as well as tumor tissue composed of those cells) was confirmed to be able to be preferably inhibited by culturing tumor cells (or tumor cells acquired from target tumor tissue) of the same type as the target tumor cells in the same manner as the HeLa cells shown in FIG. 2, and then using exosomes produced by and recovered from those cells. Consequently, expression of CD47 in the target tumor cells can be inhibited while reducing the risk of the occurrence of an immune reaction. On the other hand, as is clear from FIG. 4B, cell viability resulting from the supply of exosomes was not high with respect to A431 cells. Thus, in the present test, the suitable amount of exosomes added (concentration in medium) was determined to be about 20 μg/mL or more (and for example, 20 μg/mL to 100 μg/mL).

Figure 5A:
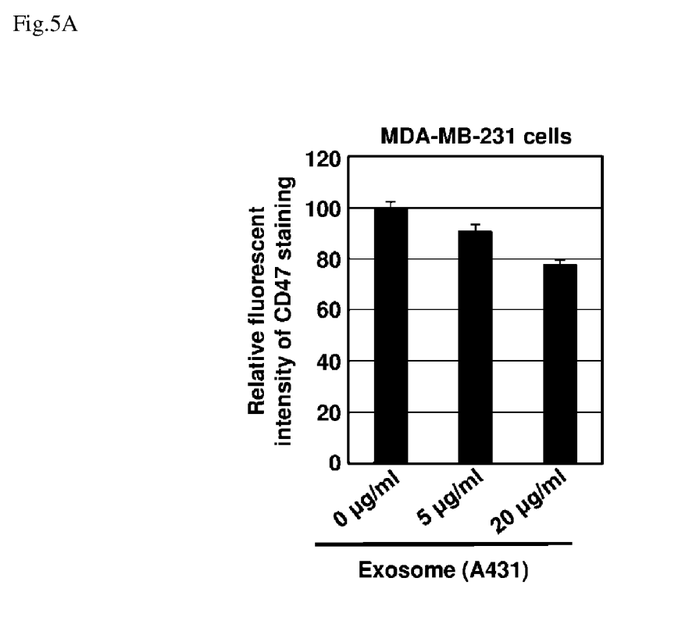
FIG. 5A is a graph investigating changes in the amount of CD47 produced after having added exosomes recovered from cultured tumor cells (A431 cells) to target tumor cells (cultured MDA-MB-231 cells); in this graph, results for each concentration of exosomes (0 μg/mL, 5 μg/mL, 20 μg/mL) added during culturing of the target tumor cells (cultured MDA-MB-231 cells) are indicated as relative fluorescent intensity (relative value based on an intensity of 100 for an exosome non-addition group (0 μg/mL)) based on the fluorescent antibody method using anti-CD47 antibody, and average values when the same tests were independently repeated three times are indicated with the bars, and the error bars indicate standard deviation (±SD).
Figure 5B:
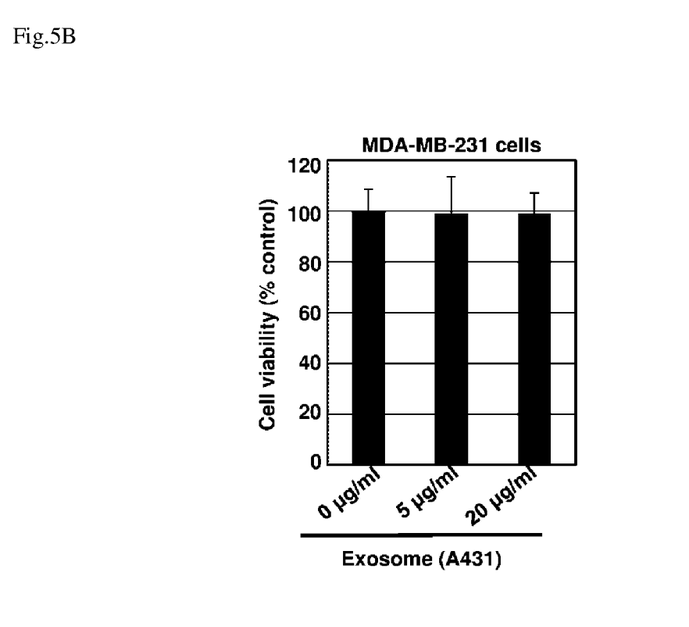
FIG. 5B is a graph investigating cell viability (%) after having added exosomes recovered from cultured tumor cells (A431 cells) to target tumor cells (cultured MDA-MB-231 cells); in this graph, results for each concentration of exosomes (0 μg/mL, 5 μg/mL, 20 μg/mL) added during culturing of the target tumor cells (cultured MDA-MB-231 cells) are indicated as a relative value based on viability of 100% for the cell viability for an exosome non-addition group (0 μg/mL), and average values when the same tests were independently repeated three times are indicated with the bars, and the error bars indicate standard deviation (±SD).

Next, FIG. 5A is a graph investigating changes in the amount of CD47 produced (expressed) after having added exosomes derived from the A431 cells of (2) to cultured MDA-MB-231 cells. FIG. 5B is a graph investigating cell viability (%) after having added exosomes derived from the A431 cells of (2) to cultured MDA-MB-231 cells.

As is clear from the results indicated in these graphs, MDA-MB-231 cells were also confirmed to preferably inhibit expression of CD47 in the same manner as the results shown in FIG. 4A. On the other hand, is as clear from FIG. 5B, cell viability resulting from the supply of exosomes was not high with respect to MDA-MB-231 cells. Thus, in the present test as well, the suitable amount of exosomes added (concentration in medium) was determined to be about 20 μg/mL or more (and for example, 20 μg/mL to 100 μg/mL).

As has been described above, according to the technology disclosed herein, expression of CD47 by target tumor cells (as well as tissue composed of those cells) can be effectively inhibited. Consequently, according to the pharmaceutical composition and method for inhibiting expression of CD47 disclosed herein, the efficacy of cancer immunotherapy against tumor cells can be improved.

What is claimed is:

1. A pharmaceutical composition for inhibiting expression of CD47 in target tumor cells in vitro, the pharmaceutical composition comprising:
   exosomes produced by cultured A431 cells; and
   a pharmaceutically acceptable medium,
   wherein an amount of exosomes in the pharmaceutically acceptable medium is 5 μg/mL to 50 μg/mL.

2. The pharmaceutical composition according to claim 1, wherein the exosomes are isolated from a culture broth of the cultured A431 cells by ultracentrifugation.

3. A method for inhibiting expression of CD47 in target cultured tumor cells in vitro, the method comprising the steps of:
   culturing the target tumor cells in vitro;
   producing exosomes by separately culturing A431 cells in vitro and recovering the exosomes isolated from the culture of the A431 cells by ultracentrifugation; and
   supplying the recovered exosomes to the target cultured tumor cells in an amount effective for inhibiting expression of CD47, wherein the recovered exosomes are supplied to the target cultured tumor cells so that the exosome concentration in the medium of the target cultured tumor cells is made to be at least 5 μg/mL.

4. The method for inhibiting expression of CD47 according to claim 3, wherein the target tumor cells are any of squamous cell carcinoma cells and uterine cancer cells.

5. The method for inhibiting expression of CD47 according to claim 3, wherein the target tumor cells are Hela cells or A431 cells.

6. The method for inhibiting expression of CD47 according to claim 3, wherein the recovered exosomes are supplied to the target cultured tumor cells so that the exosome concentration in the medium of the target cultured tumor cells is made to be 5 μg/mL to 100 μg/mL.

* * * * *